(12) United States Patent
Porzio et al.

(10) Patent No.: US 6,790,453 B2
(45) Date of Patent: Sep. 14, 2004

(54) ENCAPSULATION COMPOSITIONS AND PROCESS FOR PREPARING THE SAME

(75) Inventors: Michael A. Porzio, Monkton, MD (US); Dmitriy Zasypkin, Cockeysville, MD (US)

(73) Assignee: McCormick & Company, Inc., Sparks, MD (US)

( * ) Notice: Subject to any disclaimer, the term of this patent is extended or adjusted under 35 U.S.C. 154(b) by 0 days.

(21) Appl. No.: 10/096,665

(22) Filed: Mar. 14, 2002

(65) Prior Publication Data

US 2002/0189493 A1 Dec. 19, 2002

Related U.S. Application Data

(60) Provisional application No. 60/275,484, filed on Mar. 14, 2001.

(51) Int. Cl.$^7$ .......................... A01N 25/10; A61K 9/48
(52) U.S. Cl. ...................... 424/408; 424/400; 424/405; 424/406; 424/439; 424/440; 424/441; 424/442; 424/484; 424/485; 514/774; 514/777; 514/778; 514/779; 514/780; 514/781; 514/782
(58) Field of Search .............................. 424/400, 401, 424/405, 408–410, 439–442, 484–485, 739; 574/774, 777–782

(56) References Cited

U.S. PATENT DOCUMENTS

| | | |
|---|---|---|
| 2,809,895 A | 10/1957 | Swisher |
| 2,857,281 A | 10/1958 | Schultz et al. |
| 3,041,018 A | 6/1962 | Brooke-Smith |
| 3,041,180 A | 6/1962 | Swisher et al. |
| 3,314,803 A | 4/1967 | Dame et al. |
| 3,704,137 A | 11/1972 | Beck |
| 3,971,852 A | 7/1976 | Brenner et al. |
| 4,230,687 A | 10/1980 | Sair et al. |
| 4,420,534 A | 12/1983 | Matsui et al. |
| 4,515,769 A * | 5/1985 | Merritt et al. ............... 424/49 |
| 4,532,145 A | 7/1985 | Saleeb et al. |
| 4,689,235 A | 8/1987 | Barnes et al. |
| 4,707,367 A | 11/1987 | Miller et al. |
| 4,820,534 A | 4/1989 | Saleeb et al. |
| 5,009,900 A | 4/1991 | Levine et al. |
| 5,087,461 A | 2/1992 | Levine et al. |
| 5,124,162 A | 6/1992 | Boskovic et al. |
| 5,601,760 A | 2/1997 | Rosenberg |
| 5,603,971 A | 2/1997 | Porzio et al. |

(List continued on next page.)

OTHER PUBLICATIONS

H.B. Heath, *Source Book of Flavors*, Avi Publishing Co. Inc., Westport, Connecticut, pp. 148–287 (1981).
Kirk–Othmer, *Encyclopedia of Chemical Technology*, 3$^{rd}$ Ed., vol. 13, Wiley, New York, pp. 413–485 (1981).
Kirk–Othmer, *Encyclopedia of Chemical Technology*, 3$^{rd}$ Ed., vol. 18, Wiley, New York, pp. 305–308 (1982).
Kirk–Othmer, *Encyclopedia of Chemical Technology*, 3$^{rd}$ Ed., vol. 24, Wiley, New York, pp. 1–227 (1984).
M. Glicksman, *Gum Technology in the Food Industry*, Academic Press, Inc., New York, pp. 359–397 (1969).
Kirk–Othmer, *Encyclopedia of Chemical Technology*, 3$^{rd}$ Ed., vol. 11, Wiley, New York, pp. 146–163 (1980).
Kirk–Othmer, *Encyclopedia of Chemical Technology*, 3$^{rd}$ Ed., vol. 11, Wiley, New York, pp. 490–498 (1980).
Kirk–Othmer, *Encyclopedia of Chemical Technology*, 3$^{rd}$ Ed., vol. 12, Wiley, New York, pp. 297–351 (1980).
H. Levine, et al., "Water as a Plasticezer: physico–chemical aspects of low moisture polymeric systems," in *Water Science Reviews*, vol. 3, F. Franks, Ed., Cambridge University Press, London, pp. 79–185 (1988).
V.P. Yuryev, et al., *Carbohydrate Polymers*, vol. 15, pp. 243–253 (1991).
H. Levine, et al., "Glass Transitions in Foods," in *Physical Chemistry of Foods*, H. Schwartzberg and R. Martel, Eds., Marcel Dekker, Inc., New York, pp. 83–221, (1992).
D.V. Zasypkin, et al., *Carbohydrate Polymers*, vol. 18, pp. 119–124 (1992).
Kirk–Othmer, *Encyclopedia of Chemical Technology*, 4$^{th}$ Ed., vol. 2, Wiley, New York, pp. 854–1018 (1992).
R.L. Whistler, *Industrial Gums*, 3$^{rd}$ Ed., Chap. 11, Academic Press, Inc., New York, pp. 295–308 (1993).
R.L. Whistler, *Industrial Gums*, 3$^{rd}$ Ed., Chap. 12, Academic Press, Inc., New York, pp. 309–339 (1993).
Kirk–Othmer, *Encyclopedia of Chemical Technology*, 4$^{th}$ Ed., vol. 11, Wiley, New York, pp. 805–833 (1994).
Kirk–Othmer, *Encyclopedia of Chemical Technology*, 4$^{th}$ Ed., vol. 12, Wiley, New York, pp. 204–227 (1994).
Kirk–Othmer, *Encyclopedia of Chemical Technology*, 4$^{th}$ Ed., vol. 13, Wiley, New York, pp. 73–136 (1995).
Kirk–Othmer, *Encyclopedia of Chemical Technology*, 4$^{th}$ E., vol. 14, Wiley, New York, pp. 524–602 (1995).
Kirk–Othmer, *Encyclopedia of Chemical Technology*, 4$^{th}$ Ed., vol. 24, Wiley, New York, pp. 830–831 (1997).
Kirk–Othmer, *Encyclopedia of Chemical Technology*, 4$^{th}$ Ed., vol. 25, Wiley, New York, pp. 1–17 (1998).
Kirk–Othmer, *Encyclopedia of Chemical Technology*, 4$^{th}$ Ed., vol. 14, Wiley, New York, pp. 524–602 (1995).
Kirk–Othmer, *Encyclopedia of Chemical Technology*, 3$^{th}$ Ed., vol. 13, Wiley, New York, pp. 313–185 (1981).
Kirk–Othmer, *Encyclopedia of Chemical Technology*, 4$^{th}$ Ed., vol. 24, Wiley, New York, pp. 830–831 (1997).
Kirk–Othmer, *Encyclopedia of Chemical Technology*, 3$^{rd}$ Ed., vol. 18, Wiley, New York, pp. 305–308 (1982).

*Primary Examiner*—Neil S. Levy
(74) *Attorney, Agent, or Firm*—Oblon, Spivak, McClelland, Maier & Neustadt, P.C.

(57) ABSTRACT

Encapsulation compositions in which an encapsulate (A) is encapsulated in a matrix (B) may be prepared by:
  (i) mixing matrix (B) with a liquid plasticizer and encapsulate (A) in an extruder, to obtain a melted mixture of encapsulate (A) and matrix (B); and
  (ii) extruding the melted mixture, to obtain an extruded mixture.

28 Claims, No Drawings

U.S. PATENT DOCUMENTS

| | | |
|---|---|---|
| 5,756,136 A | 5/1998 | Black et al. |
| 5,897,897 A | 4/1999 | Porzio et al. |
| 5,972,395 A | 10/1999 | Saleeb et al. |
| 6,077,559 A | 6/2000 | Logan et al. |
| 6,090,419 A | 7/2000 | Popplewell et al. |
| 6,187,351 B1 | 2/2001 | Porzio et al. |
| 6,245,366 B1 | 6/2001 | Popplewell et al. |
| 6,416,799 B1 | 7/2002 | Porzio et al. |
| 6,444,246 B1 | 9/2002 | Popplewell et al. |
| 6,652,895 B2 | 11/2003 | Porzio et al. |

* cited by examiner

ENCAPSULATION COMPOSITIONS AND PROCESS FOR PREPARING THE SAME

CROSS REFERENCES TO RELATED APPLICATIONS

This application claims priority to U.S. Provisional Patent Application No. 60/275,484, filed on Mar. 14, 2001, and which is incorporated herein by reference in its entirety.

BACKGROUND OF THE INVENTION

1. Field of the Invention

The present invention relates to encapsulation compositions in which an encapsulate is encapsulated in a glassy matrix. More particularly, the present invention relates to flavor encapsulation compositions in which a flavoring agent is encapsulated in a glassy matrix. The present invention further relates to processes for preparing such compositions.

2. Discussion of the Background

The encapsulation of encapsulates is an area of active research. In particular, the encapsulation of encapsulates such as medications, pesticides (including insecticides, nematocides, herbicides, fungicides, microbicides etc.) preservatives, vitamins and flavoring agents is desired for a number of reasons. In the case of medications and pesticides, encapsulation may be desired to achieve the controlled release of the medication or pesticide. In the case of vitamins, encapsulation may be carried out to protect the vitamin from air-oxidation and, thus, to extend shelf life of the vitamin. In the case of the flavoring agent, the encapsulation may be carried out to place the flavoring in an easily metered form which will release the agent at a controllable event, such as the addition of water.

It is generally known to skilled practitioners in the field of flavor encapsulation that the current practical commercial processes leading to stable, dry flavors are limited to spray drying and extrusion fixation. The former process requires emulsification or solubilization of the flavor in an aqueous carrier containing the encapsulation solids, followed by rapid drying in a high temperature, high velocity gas stream and collection as a low density bulk solid.

While spray drying accounts for the majority of commercially encapsulated flavor materials, several limitations of the process are evident. Low molecular weight components of complex or natural flavor mixtures generally exhibit high vapor pressures and are usually lost or disproportionate during the process. The resultant flavor-carriers are porous and difficult to handle. In addition, deleterious chemical reactions such as oxidation can result on surfaces exposed during and after drying. The final product, a dry, free flowing powder, will release the encapsulant rapidly upon hydration whether rapid release is desired or not.

U.S. Pat. No. 3,971,852 discloses the use modified starch, gums and other food polymers with low molecular weight polyhydroxy compounds with spray drying to yield a glassy matrix with encapsulated oil at a maximum of 70–80% by volume. The system forms a shell surrounding the oil flavoring but is limited to lipophilic flavoring agents.

U.S. Pat. No. 4,532,145, discloses a process for preparing compositions in which a volatile flavorant is fixed by spray drying from a carrier solution made up of 10–30% of a low molecular weight component such as a sugar or edible food acid with the balance of the solids being a maltodextrin carbohydrate in the amount of 70–90%.

U.S. Pat. No. 5,124,162 discloses a carrier mixture composed of mono- and disaccharides (22–45%), maltodextrins (25–50%), and a high molecular weight carbohydrate such as chemically modified starch, gum arabic or gum acacia (10–35%) to which flavoring agents are added and the subsequent solution spray dried to yield a free flowing powder with a bulk density of 0.50 g/cc.

U.S. Pat. No. 5,601,760 discloses a carrier mixture utilizing whey protein isolates to encapsulate lipid flavor systems. The protein constitutes 35 to 100% of the encapsulating matrix with the remainder consisting of sugars. Other disclosed proteins include whey protein concentrates, β-lactoglobulin and α-lactoalbumin.

Several technical issues unmet by these approaches are evident. First thermally sensitive flavors undergo undesirable reactions including oxidations, rearrangements and hydrolyses. Secondly, volatile components are lost or disproportionate during atomization and evaporation in the dryer.

A second process route, that of melt encapsulation has been utilized to advantage with lipid-based flavors. In this technology, a melt is prepared by boiling off sufficient water from a high solids carbohydrate syrup, adding flavoring oils with emulsifier, agitating under pressure to emulsify the oil in the melt and injecting the mixture into a chilling, dehydrating solvent bath to obtain fine rod-like filaments. After solvent removal, the matrix is reduced in size and, in some cases, coated with an anti-caking agent before being packed. See, e.g., U.S. Pat. Nos. 2,809,895; 3,041,018; 2,856,291; 2,857,821; and 3,704,137. Subsequent improvements in the art are disclosed in U.S. Pat. No. 3,314,803, for the encapsulation of volatiles such as acetaldehyde, and in U.S. Pat. No. 4,707,367, which discloses encapsulation of up to 35% by weight flavor oil in the glassy matrix.

U.S. Pat. No. 4,689,235 discloses the use of modified starch-maltodextrin carriers in the range of 5 parts modified starch:95 parts maltodextrin to 95 parts modified starch:5 parts maltodextrin. The carrier is dissolved to form a syrup, the water is cooked off, flavor is added and emulsified, and the melt is injected into a solvent bath.

An alternative route to encapsulating flavors is disclosed in U.S. Pat. No. 4,230,687. In this approach, high molecular weight carriers such as proteins, starches and gums are plasticized by addition of significant amounts of water in the presence of the encapsulate and subjected to a high shear dispersing process. The rubbery or plastic matrix with encapsulate is then extruded, recovered and dried to yield a stable product.

Another alternative process, melt extrusion, can be utilized for flavor fixation and encapsulation. In this process, a melting system, i.e. an extruder, is employed to form the carrier melt in a continuous process. The encapsulated flavor is either admixed or injected into the molten carbohydrate carrier. U.S. Pat. No. 4,420,534 discloses the use of a matrix composition consisting of 10–30% of a low molecular weight component chosen from a series of mono- and disaccharides, corn syrup solids, or organic acid with a balance of the mixture being maltodextrin. The matrix is dry blended with an anhydrous liquid flavoring component and melted in a single screw extruder to yield a solid matrix characterized as a glass with a glass transition temperature greater than 40° C.

U.S. Pat. No. 5,972,395 discloses use of a matrix composed of 15 to 40% of a high molecular weight carrier, preferably a maltodextrin and at least 40% of a low molecular weight carbohydrate, sugar polyol or adipic acid. The matrix is extruded to yield a solid matrix characterized as a glass.

U.S. Pat. Nos. 5,087,461 and 5,009,900 disclose a similar approach utilizing a composition consisting of a modified food starch, maltodextrin, polyol and mono- and disaccharide components. The starch is a chemically modified water-soluble starch and is used in the amount of 40 to 80% of the total mixture. The balance of the composition is comprised of 10 to 40% maltodextrin, 5 to 20% corn syrup solids or polydextrose and 5 to 20% mono- or disaccharide. This matrix is made to balance processing response with glass matrix character.

U.S. Pat. Nos. 6,187,351, 5,603,971, and 5,987,897 disclose the use of a series of matrix compositions utilizing modified starch with mono- or disaccharides, modified starch with polyol, and food polymer plus carbohydrates. The use of water to plasticize the matrix in the extrusion process yields an encapsulated flavor matrix characterized by glass transition temperatures greater than 40° C. In U.S. Pat. No. 6,187,351, the use of 2 to 45% of a food polymer, 25 to 80% of a maltodextrin, and 10 to 30% of a mono- or disaccharide or 24 D.E. to 42 D.E. corn syrup solids is disclosed. The matrix is dry blended, fed into the extruder with the required water plasticizer and flavor, and the resulting encapsulate is obtained as a glassy solid exhibiting a glass transition temperature greater than 40° C. The disclosed polymers include modified celluloses, high methoxy pectin, gum arabic (acacia), locust bean gum, guar gum, and lesser gums such as gum ghatti, gum tragacanth and gum karaya. Also disclosed are proteins such as gelatin and α-casein, microbial gums such as xanthan and gellan, pregelatinized starches in addition to other carbohydrate polymers such as inulins, β-glucans and konjac flour.

U.S. Pat. No. 5,756,136 discloses the encapsulation of cinnamic aldehyde in a matrix containing at least 25% of a whey protein isolate. The resulting encapsulate exhibits a control release functionality and protection for yeast-leavened dough.

SUMMARY OF THE INVENTION

In a number of the cited patents teaching melt extrusion, matrix compositions were carefully defined to accommodate processing limitations of the extruder as well as to generate a stable matrix being in the glassy state and characterized by a glass transition temperature of greater than 40° C.

Formation of a matrix in the glassy state is of particular value for encapsulation of water-soluble flavorings and extracts. The role of water as a plasticizing agent conflicts with the desired results, because water has the effect of lowering the glass transition temperature (Tg) of the glassy matrix. In model studies of a number of food carbohydrate systems, the upper limit of water content is approximately 7–10 wt. % for lower molecular weight components such as mono- and disaccharides, maltodextrins and combinations of these agents. At higher water contents, the Tg is lowered to the extent that the matrix is in the undesirable rubbery, plastic or fluid state at room temperatures.

In order to insure higher Tg's there are several options available. By limiting the class of encapsulate materials to lipophilic materials such as citrus oils, plasticizing moisture can be removed by a boil off process as described in U.S. Pat. Nos. 2,856,291; 2,857,821; 2,809,895; 3,041,018; 3,314,803; 3,704,137; and 4,707,367. Alternatively, the use of melt encapsulation disclosed in U.S. Pat. No. 4,420,534 limits the flavoring agents to materials with lower vapor pressure which can be admixed to the premelt composition. In addition, flavorings which are in the form of aqueous extracts, water and alcohol-water solutions will result in a product with a Tg much below 25° C. leading to plastic flow and loss of volatiles upon storage.

Similarly, in U.S. Pat. Nos. 5,009,900 and 5,972,395, the flavorings are limited to those with limited volatility and total moisture level in the product is less than 11% by weight. Many of the key topnotes and unique flavor components of complex flavors have high vapor pressures at room temperature and are not easily encapsulated by such a process.

Matrix improvements for the continuous melt extrusion process are described in U.S. Pat. Nos. 6,187,351, 5,603,971 and 5,987,897. The use of modified starch and food polymers with low molecular weight carbohydrate plasticizers is detailed to yield encapsulates in a glassy matrix with greater than 40° C. However with these matrices the flavor loads are generally limited to 10 wt. % or less.

Preparation of a solid in the glassy state is dependent upon both matrix composition and the process used to generate the encapsulating material. The advantage of retaining the glass form of the matrix is increased physical stability of the solid, reduced loss of incorporated volatiles, and reduction of deleterious intermolecular reactions and oxidation. A detailed discussion of the physical chemistry of water-food polymer interactions relating to the glassy state can be found in H. Levine and L. Slade, "Glass Transitions in Foods," in *Physical Chemistry of Foods*, H. Schwartzberg and R. Hartel, Eds., Marciel Dekker, New York, pp. 83–205, 1992; and in H. Levine and L. Slade, "Water as a Plasticizer: physico-chemical aspects of low-moisture polymeric systems," in *Water Science Reviews*, vol. 3, F. Franks, Ed. Cambridge University Press, London, pp. 79–185, 1988, which are incorporated herein by reference. The role of water as a plasticizer with food polymers, as well as the relationships between molecular compositions and dynamics of interactions between various components, are discussed in these references.

Thus, there remains a need for encapsulation compositions in which an encapsulate is encapsulated in a matrix which is stable in the glass state at ambient temperatures. In particular, there remains a need for flavor encapsulation compositions in which the flavoring agent is encapsulated in a matrix which is stable in the glassy state at room temperature, i.e. has a Tg sufficiently high to prevent caking and plastic flow at ambient room temperatures. There also remains a need for a flavor encapsulation compositions which exhibit increased flavor loads with minimal surface oil levels. There also remains a need for flavor encapsulation compositions which have a high Tg and are amenable for encapsulating volatile and sensitive flavor components. There also remains a need for processes for preparing such compositions.

Accordingly, it is one object of the present invention to provide novel encapsulation compositions.

It is another object of the present invention to provide novel encapsulation compositions in which an encapsulate is encapsulated in a matrix which is stable in the glassy state at ambient temperatures.

It is another object of the present invention to provide novel flavor encapsulation compositions in which a flavoring agent is encapsulated in a matrix that is stable in the glassy state at ambient temperatures.

It is another object of the present invention to provide novel flavor encapsulation compositions which are amenable to the encapsulation of volatile or sensitive flavor components.

It is another object of the present invention to provide novel flavor encapsulation compositions which exhibit increased loads of flavor oils.

It is another object of the present invention to provide novel flavor encapsulation compositions which exhibit low surface oil levels.

These and other objects, which will become apparent during the following detailed description, have been achieved by the inventors' discovery that it is possible to prepare food polymer based glassy matrices, which have sufficiently high Tg to prevent plastic flow and caking at ambient temperatures, by interacting one or more food polymers with an aqueous plasticizer in the melting zone of an extruder and extruding the resulting mixture.

The inventors have also discovered that a composition comprising:

(A) an encapsulate, encapsulated in:

(B) a glassy matrix, said matrix comprising:

(a) 50 to 100% by weight, based on the total weight of said matrix (B), of gum arabic and 0 to 50% by weight, based on the total weight of said matrix (B), of a low molecular weight carbohydrate or polyol; or (b) 50 to 100% by weight, based on the total weight of said matrix (B), of hydrolyzed gelatin and 0 to 50% by weight, based on the total weight of said matrix (B), of a low molecular weight carbohydrate or polyol; or (c) 50 to 90% by weight, based on the total weight of said matrix (B), of a 50 to 75 Bloom gelatin and 10 to 50% by weight, based on the total weight of said matrix (B), of a low molecular weight carbohydrate or polyol; or (d) 50 to 100% by weight, based on the total weight of said matrix (B), of larch gum and 0 to 50% by weight, based on the total weight of said matrix (B), of a low molecular weight carbohydrate or polyol; or (e) 50 to 100% by weight, based on the total weight of said matrix (B), of a mixture of at least two food polymers selected from the group consisting of gum arabic, hydrolyzed gelatin, gelatin, and larch gum and 0 to 50% by weight, based on the total weight of said matrix (B), of a low molecular weight carbohydrate or polyol, are stable in the glassy state, i.e., have a sufficiently high Tg to prevent plastic flow and caking at ambient temperature.

The inventor have also discovered that the present encapsulation compositions may be prepared by a process comprising:

(i) mixing matrix (B) with a liquid plasticizer and encapsulate (A) in an extruder, to obtain a melted mixture comprising encapsulate (A) and matrix (B); and (ii) extruding said melted mixture.

DETAILED DESCRIPTION OF PREFERRED EMBODIMENTS

As noted above, the present invention has been made possible in part, by the inventors' discovery that it is possible to prepare food polymer-based matrices which contain at least 50% by weight, based on the weight of the matrix ingredients, of food polymer in the matrix composition, which have sufficiently high Tg such that the glassy matrix is stable at ambient temperatures, with the use of aqueous plasticizer. Thus the inventors have discovered that with the use of aqueous plasticizer it is possible to prepare a matrix containing over 50% by weight of a food polymer which does not undergo plastic flow or caking at ambient temperatures. This discovery is a surprising result considering the well-known large glass-transition-lowering effect of water in carbohydrate and protein based systems. Accordingly, before the present invention, one skilled in the art would not have expected that a stable glassy carbohydrate- or protein-based food polymer could have been practically prepared using an aqueous plasticizer.

Thus, in a first embodiment, the present invention provides active agent encapsulation compositions in which (A) an encapsulate is encapsulated in (B) a glassy matrix comprising:

(a) 50 to 100% by weight, based on the total weight of said matrix (B), of gum arabic and 0 to 50% by weight, based on the total weight of (a), of a low molecular weight carbohydrate or polyol; or (b) 50 to 100% by weight, based on the total weight of said matrix (B), of hydrolyzed gelatin and 0 to 50% by weight, based on the total weight of said matrix (B), of a low molecular weight carbohydrate or polyol; or (c) 50 to 90% by weight, based on the total weight of said matrix (B), of a 50 to 75 Bloom gelatin and 10 to 50% by weight, based on the total weight of said matrix (B), of a low molecular weight carbohydrate or polyol; or (d) 50 to 100% by weight, based on the total weight of said matrix (B), of larch gum and 0 to 50% by weight, based on the total weight of said matrix (B), of a low molecular weight carbohydrate or polyol; or (e) 50 to 100% by weight, based on the total weight of said matrix (B), of a mixture of at least two food polymers selected from the group consisting of gum arabic, hydrolyzed gelatin, gelatin, and larch gum and 0 to 50% by weight, based on the total weight of said matrix (B), of a low molecular weight carbohydrate or polyol.

The term encapsulate as used in the present invention, includes agents such as medications, pesticides, preservatives, vitamins, food acids, salts, flavoring agents, perfumery chemicals and fragrances, and food colorants both synthetic and natural. Suitable medications include antacids, anti-inflammatory substances, coronary vasodilators, cerebral vasodilators, peripheral vasodilators, anti-infectives, psychotropics, anti-manics, stimulants, antihistamines, laxative, decongestants, vitamins, gastrointestinal sedatives, antidiarrheal preparations, antianginal drugs, antiarrhythmics, antihypertensive drugs, vasoconstrictors, migraines treatments, anticoagulants, antithrombotic drugs, analgesics, antipyretics, hypnotics, sedatives, antiemetics, antinauseants, anticonvulsants, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucolytics, antiuricemic drugs and other drug substances such as topical analgesics, local anesthetics and the like.

Suitable pesticides include insecticides, nematocides, fungicides, herbicides, and microbicides. Insecticides, which may be encapsulated in the present compositions include those disclosed in *Kirk-Othmer, Encyclopedia of Chemical Technology*, $4^{th}$ Ed., vol. 14, Wiley, New York, pp. 524–602, 1995, and $3^{rd}$ Ed., vol. 13, pp. 313–485, 1981, both of which are incorporated herein by reference. Suitable nematocides include, e.g., methyl N'N'-dimethyl-N-[(methylcarbamox)oxy]-1-thiooxamimidate (oxamyl) and those disclosed in *Kirk-Othmer, Encyclopedia of Chemical Technology*, $4^{th}$ Ed., vol. 24, Wiley, New York, pp. 830–831, 1997, and $3^{rd}$ Ed., vol. 18, pp. 305–308(1982), both of which are incorporated herein by reference. Suitable fungicides include those disclosed in *Kirk-Othmer, Encyclopedia of Chemical Technology*, $4^{th}$ Ed., vol. 12, Wiley, New York, pp. 204–227, 1994, and $3^{rd}$ Ed., vol. 11, pp. 490–498, 1980, both of which are incorporated herein by reference. Suitable herbicides include those disclosed in *Kirk-Othmer, Encyclopedia of Chemical Technology*, 4$^{th}$ Ed., vol. 13, Wiley, New York, pp. 73–136, 1995, and 3$^{rd}$ Ed., vol. 12, pp. 297–351, 1980, both of which are incorporated herein by reference. Suitable antibiotics and antimicrobials include those disclosed in *Kirk-Othmer, Encyclopedia of Chemical Technology*, 4$^{th}$ Ed., vol. 2, Wiley, New York, pp. 854–1018 (1992), and vol. 3, pp. 1–346(1992), both of which are incorporated herein by reference. Suitable vitamins include those disclosed in *Kirk-Othmer, Encyclopedia of Chemical Technology*, 4Ed., vol. 25, Wiley, New York, pp. 1–17, 1998, and 3$^{rd}$ Ed., vol. 24, pp. 1–277, 1984, both of which are incorporated herein by reference. Suitable food additives, in addition to flavoring agents, include those disclosed in *Kirk-Othmer, Encyclopedia of Chemical Technology*, 4$^{th}$ Ed., vol. 11, Wiley, New York, pp. 805–833, 1994, and 3$^{rd}$ Ed., vol. 11, pp. 146–163, 1980, both of which are incorporated herein by reference.

The term flavoring agent includes spice oleoresins and oils derived from allspice, basil, capsicum, cinnamon, cloves, cumin, dill, garlic, marjoram, nutmeg, paprika, black pepper, rosemary and turmeric; essential oils: anise oil, caraway oil, clove oil, eucalyptus oil, fennel oil, garlic oil, ginger oil, peppermint oil, onion oil, pepper oil, rosemary oil, and spearmint oil; citrus oils such as orange oil, lemon oil, bitter orange oil and tangerine oil; alliaceous flavors: garlic, leek, chive, and onion; botanical extracts: arnica flower extract, chamomile flower extract, hops extract, and marigold extract; botanical flavor extracts: blackberry, chicory root, cocoa, coffee, kola, licorice root, rose hips, sassaparilla root, sassafras bark, tamarind and vanilla extracts; protein hydrolysates: hydrolyzed vegetable protein (HVP'S), meat protein hydrolysates, milk protein hydrolysates; and compounded flavors both natural and artificial including those disclosed in S. Heath, *Source Book of Flavors*, Avi Publishing Co. Westport, Conn., pp. 149–277, 1981, which is incorporated herein by reference. Representative flavor compounds are for example: benzaldehyde, diacetyl (2,2-butanedione), vanillin, ethyl vanillin and citral (3,7-dimethyl-2,6-octadienal). The flavoring agent may be in the form of an oil, aqueous solution, non-aqueous solution or an emulsion. Flavor essences, i.e. the water-soluble fraction derived from fruit or citrus can be utilized although at lower levels than the ingredients referenced above. As will be described more fully below, the present invention is particularly advantageous when the flavoring agent is itself a volatile compounds with varying vapor pressures at ambient conditions When the encapsulate is lipophilic, the encapsulate is dispersed in the glassy matrix of the final product usually with the aid of an emulsifier added to the lipophilic phase or in the matrix mixture.

Although the exact amount of encapsulate encapsulated in the matrix will depend, in part, upon the precise nature of the matrix, and the anticipated end use of final composition, the encapsulation compositions of the present invention will typically comprise 4 to 18% by weight, based on the total weight of the composition, of encapsulate. Preferably, the present encapsulation compositions will comprise 9 to 16% by weight, based on the total weight of the composition, of encapsulate. It is preferred that the encapsulate is a flavoring agent.

In addition to the foregoing encapsulates, various optional ingredients such as conventionally used in the art, may be included in the compositions of the present invention. For example, colorings, sweeteners, food acids, salts, fragrances, diluents, fillers, preservatives, anti-oxidants, stabilizers, lubricants, and the like may be employed herein if desired.

As noted above, the encapsulate is encapsulated in a glassy matrix of one of (a), (b), (c), (d), or (e). In all the following descriptions of the matrices (a), (b), (c), (d), and (e) all % by weight values are based upon the total weight of matrix (B).

In the following descriptions, the term food polymer will be used to characterize the major component of the encapsulating matrix. The food polymers herein referred to are specifically gelatin, gum arabic, larch gum arabinogalactan and hydrolyzed gelatin. Modified starch, specifically n-octenylsuccinate modified starch, may also be considered to be a food polymer but is not considered as such for the purposes of the present invention. The various forms of carbohydrate materials range from high molecular weight starches through the hydrolysis oligomers, the maltodextrins, to the lower molecular weight corn syrup solids and ultimately mono- and disaccharides. The maltodextrins may be considered as food polymers, however, they are not used in that context in the present invention.

In one embodiment, the glass matrix comprises (a) 50 to 100% by weight, based on the total weight of the matrix (B), of gum arabic and 0 to 50% by weight, based on the total weight of the matrix (B), of a low molecular weight carbohydrate or polyol. Preferably in embodiment (a), the glass matrix comprises (a) 50 to 99% by weight, based on the total weight of the matrix (B), of gum arabic and 1 to 50% by weight, based on the total weight of the matrix (B), of a low molecular weight carbohydrate or polyol. Even more preferably, the glass matrix comprises 60 to 80% by weight, based on the total weight of the matrix (B), of the gum arabic and 20 to 40% by weight, based on the total weight of the matrix (B), of a mono- or disaccharide.

Gum arabic is an exudate gum obtained from Acacia trees. The main species are *Acacia senegal* and *Acacia seyal*. Gum arabic is a branched molecule with a main chain of (1→3)-linked β-galactopyranosyl units having side chains, consisting of (1→3)-linked β-D-galactopyranosyl units, joined to it by (1→6)-linkages. The resulting side chains consist of various acidic sugars (see *Industrial Gums*, R. Whistler and J. BeMiller, Eds., 3$^{rd}$ Edition, Academic Press, pp. 311–318, 1993). The hydrocolloid shows enhanced solubility and relatively low viscosities in solutions of 30 to 40 wt. % solids.

Generally the *A. Senegal* gum is used to make beverage emulsions, while the *A. seyal* gum is used for spray drying applications. In spray drying, the key functional characteristics of the polymer are its emulsifying capacity, good film-forming properties upon drying and reasonably low aqueous viscosity. One key commercial specification for the *A. seyal* is the degree of color contributed by the gum. With some darker lots of the gum, a bleaching step is sometimes added to lighten the product color by oxidation. Unexpectedly it was discovered by the present inventors that only unbleached *A. seyal* or *A. Senegal* can be extruded in a manner which protects the freshly exited molten extrudate from flashing off flavor volatiles.

The selected gum arabic constitutes 50 to 100% by weight of the matrix (B). The remainder of the matrix is low molecular weight food carbohydrates and/or polyols. Suitable carbohydrates are mono- and disaccharides, invert syrups, molasses, corn syrups, and 36 to 42 D.E. corn syrup solids. Suitable polyols are erythritol, sorbitol, mannitol, lactitol, maltitol, isomalt (Palatinit®), dulcitol, xylitol, hydrogenated corn syrups, hydrogenated glucose syrups, hydrogenated maltose syrups, and hydrogenated lactose syrups. The preferred carbohydrates are glucose and maltose, and the preferred polyols are mannitol, sorbitol, and isomalt.

In another embodiment, the glass matrix comprises (b) 50 to 100% by weight, based on the total weight of said matrix (B), of hydrolyzed gelatin and 0 to 50% by weight, based on the total weight of said matrix (B), of a low molecular weight carbohydrate or polyol. Preferably in embodiment (b), the glass matrix comprises 50 to 99% by weight, based on the total weight of said matrix (B), of hydrolyzed gelatin and 1 to 50% by weight, based on the total weight of said matrix (B), of a low molecular weight carbohydrate or polyol. Even more preferably in embodiment (b), the glass matrix comprises 60 to 80% by weight, based on the total weight of the matrix (B), of the hydrolyzed gelatin and 20 to 40% by weight, based on the total weight of the matrix (B), of a polyol or a mono- or disaccharide.

In another embodiment, the glass matrix comprises (c) 50 to 90% by weight, based on the total weight of said matrix (B), of 50 to 75 Bloom gelatin and 10 to 50% by weight, based on the total weight of said matrix (B), of a low molecular weight carbohydrate or polyol. Preferably in embodiment (c), the glass matrix comprises 60 to 80% by weight, based on the total weight of the matrix (B), of the 50 to 75 Bloom gelatin and 20 to 40% by weight, based on the total weight of the matrix (B), of a polyol or a mono- or disaccharide.

Gelatin, the soluble protein extract from collagen, comes from various animal sources and in different forms. There are acid-extracted and base-extracted forms of gelatin. The key difference of the two forms being in the isoelectric point of the resultant, soluble polymer. Sources of the collagen used for extraction to generate the gelatin include cattle hides and pork skins. The type and degree of extraction lead to various grades of gelatin. Acid hydrolysis of the collagen leads to Type A acid gelatin. Similarly base hydrolysis and extraction leads to a Type B gelatin. The isoelectric points are generally in the pH range of 7 to 9 for Type A ; and 4.7 to 5.1, for Type B). Gelatins are generally characterized by their gelling strength in terms of Bloom using a standardized procedure and a Bloom gelometer. Commercial gelatins vary from 50 to 300 Bloom with the high values indicating stronger gels (see M. Glicksman, *Gum Technology in the Food Industry*, Academic Press, pp. 359–397, 1969). The particular gelatins which are most compatible with the extrusion encapsulation process of the present invention are the 50 and 75 Bloom gelatins of both type A and B.

Another form of gelatin is the hydrolyzed gelatins. These products are derived from the standard gelatin by an additional hydrolysis step. The result is a water soluble, non-gelling form of the food protein. Generally molecular weights of the hydrolyzed gelatins are in the 100,000 dalton range. Hydrolyzed gelatins are the preferred form of the gelatin for the present encapsulation matrices.

In another embodiment, the glass matrix comprises (d) 50 to 100% by weight, based on the total weight of said matrix (B), of larch gum and 0 to 50% by weight, based on the total weight of said matrix (B), of a low molecular weight carbohydrate or polyol. Preferably in embodiment (d), the glass matrix comprises 50 to 99% by weight, based on the total weight of said matrix (B), of larch gum and 1 to 50% by weight, based on the total weight of said matrix (B), of the low molecular weight carbohydrate or polyol. Even more preferably in embodiment (d), the glass matrix comprises 60 to 80% by weight, based on the total weight of the matrix (B), of the larch gum and 20 to 40% by weight, based on the total weight of the matrix (B), of a mono- or disaccharide.

In matrix (d), the food polymer is larch gum or larch arabinogalactan. These hydrocolloids are obtained from extracts of larch woods (see *Industrial Gums*, R. Whistler and J. BeMiller, Eds., 3$^{rd}$ Edition, Academic Press, p. 304, 1993). The larch arabinoglalactan hydrocolloid polymer consists of two fractions: the smaller with a molecular weight of 16,000 to 18,000 daltons, constituting approximately 80% of the mixture, and the remaining 20% with a molecular weight in the range of 80,000 to 100,000 daltons. One unique characteristic of larch gum is its very reduced solution viscosity at high total solids.

In another embodiment, the glass matrix comprises (e) 50 to 100% by weight, based on the total weight of said matrix (B), of a mixture of at least two food polymers selected from the group consisting of gum arabic, hydrolyzed gelatin, gelatin, and larch gum and 0 to 50% by weight, based on the total weight of said matrix (B), of a low molecular weight carbohydrate or polyol. Preferably in embodiment (e), the glass matrix comprises 50 to 99% by weight, based on the total weight of said matrix (B), of a mixture of at least two food polymers selected from the group consisting of gum arabic, hydrolyzed gelatin, gelatin, and larch gum and 1 to 50% by weight, based on the total weight of said matrix (B), of the low molecular weight carbohydrate or polyol. Even more preferably in embodiment (e), the glass matrix comprises 60 to 80% by weight, based on the total weight of the matrix (B), of the a mixture of at least two food polymers selected from the group consisting of gum arabic, hydrolyzed gelatin, gelatin, and larch gum and 20 to 40% by weight, based on the total weight of the matrix (B), of a mono- or disaccharide.

In embodiments (b), (c), (d), and (e), the low molecular weight carbohydrates and polyols are the same as those described above for matrix (a).

In another embodiment, the present invention provides a process for preparing the present encapsulation compositions, which comprises:

(i) mixing matrix (B) with a liquid plasticizer and encapsulate (A) in an extruder, to obtain a melted mixture comprising encapsulate(A) and matrix (B); and (ii) extruding said melted mixture.

In the present process, the liquid plasticizer may be any which is suitable for facilitating the formation of the melt in the extruder while at the same time affording a product which exists in the glassy state, rather than the plastic or rubbery state at room temperature. Suitable plasticizers include water; glycerol; propylene glycol; aqueous solutions of glycerol, propylene glycol, monosaccharides, and disaccharides; and invert and high fructose corn syrups. When the encapsulate is a flavor and the final product is intended to be used as a food additive, the plasticizer should be a food grade solvent. In one preferred embodiment, the present compositions are prepared by utilizing water as the liquid plasticizer.

The plasticizer is added in an amount which results in the formation of a melt in the extruder, while at the same time affording a product which exists in the glassy state at room temperature. Thus, the amount of the plasticizer added may be selected to afford a product which has a Tg of at least 30° C., preferably at least 35° C., more preferably at least 40° C.

The matrix (B), along with the plasticizer forms a melt in the extruder. Although the mixing action of the extruder will supply heat to the matrix/plasticizer mixture, it will typically be necessary to supply additional heat to ensure formation of the melt. The encapsulate (A) is continuously added in a liquid phase to the feeding zone of the extruder by injection and mixed with the melted matrix/plasticizer mixture before exiting the extruder. In some embodiments, it may be preferred to add a non-aqueous, liquid plasticizer may be added to the encapsulate phase.

In certain embodiments, a surface-active agent, i.e. an emulsifier can be added to the dry blend, or preferably added to the liquid flavor mix which is ultimately injected into the metering zone of the extruder. These emulsifiers can be from the class of distilled monoglycerides, mono- and diglyceride blends, propyleneglycol monoglycerides, lecithin, modified lecithins, acetylated monoglycerides, lactylated monoglycerides, lactylated propyleneglycol monoglycerides, sorbitan esters, sorbitan-polyoxyethylene [20] monoglycerides, polyglycerol esters, DATEM's (diacetyltartarate esters of monoglycerides), succinylated esters of monoglycerides and polyoxyethylenepropylene copolymers and mixtures thereof. Most preferred surfactants are the sorbitan-polyoxyethylene [20] monoglycerides, lecithins, and polyglycerol esters.

The flavorants can be compounded flavors, essential oils, citrus oils, fruit extracts and essences, oleoresins and other forms. In some cases, the flavors can be diluted in a series of flavor solvents. These include fractionated coconut oils (medium chain triglycerides), propyleneglycol, glycerol, triacetin (glycerol triacetate) among others.

In a preferred embodiment, the use of a twin screw extruder is preferred.

When the encapsulation composition exits the extruder, it may be cooled by remaining in ambient temperature air, or in chilled or subambient temperature air, or by passing through a liquid bath, with or without temperature control. Although not necessary, the cooled product may be further processed by size reduction, for example by grinding or pulverizing. The product may also be treated with a anti-agglomeration compound either before or after size reduction.

One key physical property of the flavor-containing glassy extrudate is the level of surface oil. These levels will be a function of melt process, matrix composition and die geometry. By using a fine die orifice, the resulting thin strands of extrudate will have higher surface areas and by inference increasing levels of surface oil. A series of compositions were tested for surface oil by washing the sample surface with hexane, filtering of suspended particles and reading the optical density of the solution at a chosen wavelength (usually 230 nm in the U.V.). The reading is then compared to a set of dilution standards of the same flavor in hexane. By using the corresponding correction factors, a surface oil value in grams of flavor per 100 grams of sample can be determined. The values obtained ranged from 0.0001 grams of surface oil/100 grams of sample in the best case example (for the hydrolyzed gelatin-mannitol compositions) to 0.13 grams of surface oil/100 grams of sample with gum arabic-maltose-dextrose carriers. The extremely low levels of surface oil are unexpected and allow a commercial product to be prepared without additional steps of solvent washing and desolventizing the product.

It was determined experimentally by the present inventors that only a limited number of food polymers were functional in the melt extrusion process, restricting the exiting melt from "flashing off" volatiles, to generate a glassy matrix and exhibit good flavor encapsulation capabilities. It is now a general conjecture by the present inventors that low solution viscosity of a limited number of food polymers can be used to correlate with desired melt viscosities in the extruder. It is most likely that there is a correlation between both viscosities and the average molecular weight of polymers or compact structures of polymer molecules or both. In other words, the lower the molecular weight of a polymer and the more compact structure of the polymer, the lower will be the viscosity of its solution or melt. In addition to viscosity, a lower molecular weight of the polymer will reduce elastic recovery of the material at the die exit and favor short setting times of the material thus reducing loss of volatile encapsulate.

As noted above, there are a limited number of polymers and food polymer oligomers used with the low moisture environments of the 'syrup' melt extrusion and continuous melt extrusion processes. In both of the former processes, use of a specific, chemically-modified food starch has played a dominant role. This material which is the n-octenylsuccinate derivative of dextrinized starch, is sold under the trade names of Capsul (National Starch Company) and Amiogum (Cerestar). The product could be more correctly characterized as a modified dextrin since the dextrinization process leads to average molecular weights of 30,000 to 50,000 for the carbohydrate polymer. The material advantages of excellent solubility and low solution viscosities found in the ranges of 35 to 45% dissolved solids must be balanced against the negative attributes such as the acidic character derived from the bound succinic acid groups (solution pH values in the range of 2.5–3.0) and the distinctive "cardboardy" after-taste which is results from the roasting or dextrinization step in processing the starch.

To test the hypothesis that low solution viscosity at high dissolved solids of selected food polymers can relate directly to practical extrusion melt viscosities, a series of food polymer solutions were prepared at 40% w/w total solids and 50% w/w total solids, heated to insure hydration, and equilibrated overnight. A Brookfield Viscometer, Model RVDV II was employed utilizing a spindle RV2. Readings were taken at a number of speeds. The results are given in Table I.

TABLE I

Comparative Solution Viscosities of Selected Food Polymers Using a Brookfield Model RV DV II Viscometer with Spindle RV2

| Food Polymer | Viscosity (cps) | |
|---|---|---|
| | 40% Total Solids | 50% Total Solids |
| Capsul[1] | 137 | 163 |
| Hydrolyzed Gelatin[2] | 74 | 144 |
| Gum Arabic[3] | 440 | 3500 |
| Larch Gum[4] | 48 | 107 |

[1]Capsul - n-octenylsuccinanhydride, derivativized, dextrinized corn starch; National Starch
[2]Hydrolyzed gelatin- Vyse Gelatin Company
[3]Gum arabic (spray dried), Colloides Natureles Company
[4]Larch arabinogalactan - Larex Company From the solubility-viscosity relationsips for the above polymers, it could be predicted that any additional food polymers with similar solution solubility-viscosity responses might be predicted to form glassy extrudate according to these current teachings.

Moreover it is known in the polymer and plastics industry that polymer melts can be co-soluble, or alternately, separate incompatible phases during melt extrusion. In aqueous concentrated solutions, thermodynamic incompatibility or limited co-solubility of biopolymers is a well-known phenomenon affecting structure and key functional properties of their solutions. For an aqueous solution of a pair of water-soluble biopolymers the region of co-solubility, corresponding to a relatively low concentration of both polymers, would be a single-phase, transparent solution. Above this concentration, the system will form two layers (phases) with a predominant concentration of one of the biopolymers in one of the phases. Extensive mixing of the two-phase solution would lead to a water-in-water type of emulsion. This simple scenario does not assume formation of any soluble or insoluble complexes between biopolymers when structure of the solution will be more complex. Numerous publications describe behavior of biopolymers in solutions and gels, however data is limited or non-existent for compatibility of food biopolymers in a melt. The major issue is in the high temperatures (above water boiling point) usually needed to form a biopolymer melt at low water content and high melt viscosity preventing equilibrium separation of phases.

A multiphase structure of composite biopolymer melts based on soy protein and maltodextrin has been observed with optical microscopy, SEM, X-ray and near-IR spectroscopy (see Yuryev, V. P., Zasypkin, D. V., Ghenin, Ya. V., Zhukov, V. A., Alexeyev, V. V. & Tolstoguzov, V. B., "Role of maltodextrin in promoting structure formation in extruded soya isolate," *Carbohydrate Polymers*, vol. 15, pp. 243–253 (1991)).

Composite materials have been produced by thermoplastic extrusion, by using a cooling die to suppress melt expansion and changes in structure. It was inferred that the multiphase structure resulted from incompatibility or/and kinetics of mixing of biopolymers in the melt (see Zasypkin, D. V., Yuryev V. P., Alexeev, V. V. & Tolstoguzov, V. B., *Carbohydrate Polymers*, vol. 18, pp. 119–124(1992)).

Limited co-solubility of biopolymers and multiphase structure of the blends can be expected to have a profound effect on flavor encapsulation in such mixed systems. In a general case, one polymer having a stronger affinity to a flavor and carrying most of it can be encapsulated in the continuous phase formed by the second polymer. While the inventors acknowledge that the field of food polymer-polymer melt extrusion has not been adequately reported, it appears that co-melting of mixed polymers with the addition the carbohydrate plasticizer can be achieved by the procedure described herein.

In the extrusion process, the matrix mixture contains lower molecular weight components. For the gelatin and hydrolyzed gelatin systems, polyols are preferred to avoid the Maillard browning reactions which result from the reaction of the side chain amino acids and reducing sugars. For the non-protein food polymers, the choice of low molecular weight carbohydrate is determined by the melt dynamics of the extruder. In certain cases, the monosaccharides and disaccharides can be in the form of crystalline hydrates. For glucose monohydrate the water contribution is 10% by weight of the crystalline sugar. For maltose or lactose monohydrate, that contribution falls to 5 wt. % added water. In such cases the water stream added as a plasticizer for the melt will be adjusted to compensate for the internal free water contributed by the "melting" of the water of crystallization.

Other features of the invention will become apparent in the course of the following descriptions of exemplary embodiments which are given for illustration of the invention and are not intended to be limiting thereof.

EXAMPLES

Melt extrusion was accomplished utilizing a laboratory 2" co-rotating twin-screw extruder incorporating oil jacket heating, fitted with a liquid injection port in the transfer zone of the unit, and utilizing a 0.031" multi-orifice die. A matrix consisting of preblended food polymer(s) and carbohydrate were metered into the feed port at a feed rate between 100 to 130 grams/minute of solids; the water (plasticizer) liquid stream was delivered to the feed port by a metering peristaltic pump at approximately 3–5 ml/minute The jacket temperature was set at 250° F. Two liquid flavors were prepared as concentrates: a lipid-based flavor, "lemonade," utilizing a lemon citrus oil base, and a compounded peach flavor. In some cases an emulsifier such as polysorbate 60(polyoxyethylene [20] sorbitan mono stearate) was added to the flavor at 0.5 to 5% (w/w emulsifier/flavor). In selected formulas propyleneglycol was added as a separate liquid stream or as a cosolvent with the selected flavor. After lining out the feed and conveying rates and bringing the unit into a steady-state, the extrudate was air cooled and collected in the form of fine strands which rapidly set into a brittle, glassy solid.

Example 1

A polymer matrix blend consisting of 80% by weight of hydrolyzed gelatin and 20% by weight of mannitol was prepared. The matrix was fed into the extruder, water was added to the feed port at approximately 3 to 5 ml/minute (~2 to 4% by weight of the total feed rate), and a flavor stream consisting of lemonade flavor was metered into the extruder feed zone at a rate equivalent to a flavor load of 12% by weight. The product was obtained as fine threads directly from the die which rapidly set into a glassy solid. Analyses showed that the product had a flavor load of 10.5% by weight, based on the total weight of the composition, and a Tg of 50.1° C. as determined by DSC. The surface oil of the unmilled strands was determined by a solvent wash. The product exhibited less than 0.0001% by weight, based on the total weight of the composition, of surface oil.

Example 2

A polymer matrix blend consisting of 80% by weight of hydrolyzed gelatin and 20% by weight of isomalt was prepared. The matrix was fed into the extruder, water was added to 3 to 5 ml/minute to the feed zone, and a flavor stream consisting of lemonade flavor was metered into the extruder melt zone at a flavor load level of 16% by weight. The product strains rapidly set into a glassy solid. Analyses showed the product had a flavor load of 14.6% by weight, based on the total weight of the composition, and a Tg of 55.7° C. The material exhibited <0.001% by weight, based on the total weight of the composition, of surface oil.

Example 3

A polymer matrix consisting of 100% by weight of hydrolyzed gelatin was utilized. A lemonade flavor was added at a feed rate equal to 16% by weight and the mixture was melted and obtained as a glassy solid. The flavor load analyzed by VOSD showed that the flavor load was 14.1% by weight, based on the total weight of the composition, and the Tg was 36.9° C. Surface oil was found to be <0.02% by weight, based on the total weight of the composition.

Example 4

A polymer matrix blend of 60% by weight of gum arabic, 25% by weight of maltose monohydrate, and 15% by weight of anhydrous dextrose was utilized and fed into the extruder. A lemonade flavor was added at an estimated level of 9% by weight. Analysis by VOSD showed the glassy encapsulation matrix had a flavor load of 6.3% by weight, based on the total weight of the composition, and a Tg of 39.5° C. by DSC analysis. The surface oil was found to be 0.13% by weight, based on the total weight of the composition.

Example 5

A polymer matrix consisting of 55% by weight of gum arabic, 25% by weight of hydrolyzed gelatin, and 20% by weight of mannitol was added to the extruder. A peach flavor containing propyleneglycol as a plasticizing agent and polysorbate 60 emulsifier was metered in at an estimated level of 10% by weight. A solid, glassy encapsulate was obtained. Upon analysis the material showed a Tg of 44.1° C. and a flavor load by GLC analyses of 9.3% by weight, based on the total weight of the composition (averaged over four of the key flavor components).

Example 6

A food polymer matrix consisting of 80% by weight of hydrolyzed gelatin and 20% by weight of mannitol was added to the extruder with a separate water plasticizing stream. Peach flavor containing propyleneglycol and polysorbate 60 emulsifier was added at an estimated level of 18% by weight. The encapsulate was obtain as brittle threads and showed a Tg of 39.1° C. The flavor level was determined by GLC analyses to be 12% by weight, based on the total weight of the composition.

Example 7

A food polymer matrix consisting of 80% by weight of 75Boom gelatin and 20% by weight of mannitol was added to the extruder along with a separate water plasticizing stream. A lemonade flavor containing polysorbate 60was metered into the melt zone of the extruder at an estimated level of 9% by weight. A solid was obtained with a glassy character having a Tg of 51.5° C. The flavor load was determined to be 8.7% by weight, based on the total weight of the composition, and the surface oil was 0.023% by weight, based on the total weight of the composition.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. An encapsulation composition, comprising:
   (A) an encapsulate, encapsulated in:
   (B) a glassy matrix, said matrix comprising:
      (a) 50 to 99% by weight, based on the total weight of said matrix (B), of gum arabic and 1 to 50% by weight, based on the total weight of said matrix (B), of a low molecular weight carbohydrate or polyol; or
      (b) 50 to 99% by weight, based on the total weight of said matrix (B), of a mixture of at least two food polymers selected from the group consisting of gum arabic, hydrolyzed gelatin, gelatin, and larch gum and 1 to 50% by weight, based on the total weight of said matrix (B), of a low molecular weight carbohydrate or polyol,
   wherein said low molecular weight carbohydrate or polyol is selected from the group consisting of glucose, sucrose, maltose, lactose, 42 dextrose equivalent and 36 dextrose eqivalent corn syrup solids, erythritol, lactitol, mannitol, sorbitol, maltitol, isomalt, xylitol, hydrogenated corn syrups, hydrogenated glucose syrups, hydrogenated maltose syrups, hydrogenated lactose syrups, and mixtures thereof.

2. The composition of claim 1, wherein said matrix (B) comprises:
   (a) 50 to 99% by weight, based on the total weight of said matrix (B), of gum arabic and 1 to 50% by weight, based on the total weight of said matrix (B), of a low molecular weight carbohydrate or polyol.

3. The composition of claim 2, wherein said matrix (B) comprises:
   (a) 60 to 80% by weight, based on the total weight of said matrix (B), of gum arabic and 20 to 40% by weight, based on the total weight of said matrix (B), of a low molecular weight carbohydrate or polyol.

4. The composition of claim 1, wherein said matrix (B) comprises:
   (b) 50 to 99% by weight, based on the total weight of said matrix (B), of a mixture of at least two food polymers selected from the group consisting of gum arabic, hydrolyzed gelatin, gelatin, and larch gum and 1 to 50% by weight, based on the total weight of said matrix (B), of a low molecular weight carbohydrate or polyol.

5. The composition of claim 4, wherein said matrix (B) comprises:
   (b) 60 to 80% by weight, based on the total weight of said matrix (B), of a mixture of at least two food polymers selected from the group consisting of gum arabic, hydrolyzed gelatin, gelatin, and larch gum and 20 to 40% by weight, based on the total weight of said matrix (B), of a low molecular weight carbohydrate or polyol.

6. The composition of claim 1, having a glass transition temperature of at least 35° C.

7. The composition of claim 1 wherein said encapsulate is selected from the group consisting of medications, pesticides, vitamins, preservatives, and flavoring agents.

8. The composition of claim 1, wherein said encapsulate is a flavoring agent.

9. The composition of claim 8, wherein said flavoring agent is selected from the group consisting of natural extracts, oleoresins, essential oils, protein hydrolysates, aqueous reaction flavors, compounded natural flavors, and artificial flavors.

10. The composition of claim 8, wherein said flavoring agent optionally contains a plasticizer or an emulsifier.

11. An encapsulation composition, comprising:
    (A) an encapsulate, encapsulated in:
    (B) a glassy matrix, said matrix comprising:
       (a) 50 to 99% by weight, based on the total weight of said matrix (B), of gum arabic and 1 to 50% by weight, based on the total weight of said matrix (B), of a low molecular weight carbohydrate or polyol; or
       (b) 50 to 99% by weight, based on the total weight of said matrix (B), of a mixture of at least two food polymers selected from the group consisting of gum arabic, hydrolyzed gelatin, gelatin, and larch gum and 1 to 50% by weight, based on the total weight of said matrix (B), of a low molecular weight carbohydrate or polyol,
    wherein said low molecular weight carbohydrate or polyol is selected from the group consisting of glucose, sucrose, maltose, lactose, 42 dextrose equivalent and 36 dextrose equivalent corn syrup solids, erythritol, lactitol, mannitol, sorbitol, maltitol, isomalt, xylitol, hydrogenated corn syrup, hydrogenated glucose syrups, hydrogenated maltose syrups, hydrogenated lactose syrups, and mixtures thereof, and wherein said composition is prepared by a process comprising:

(i) mixing matrix (B) with a liquid plasticizer and encapsulate (A) in an extruder, to obtain a melted mixture which comprises encapsulate (A) and matrix (B); and (ii) extruding said melted mixture, to obtain an extruded mixture.

12. The composition of claim 11, wherein said liquid plasticizer is at least one member selected from the group consisting of water; glycerol; propylene glycol; aqueous solutions of glycerol, propylene glycol, monosaccharides, and disaccharides; and invert and high fructose corn syrups; and mixtures thereof.

13. The composition of claim 11, wherein said liquid plasticizer is water.

14. The composition of claim 11, further comprising cooling said extruded mixture.

15. The composition of claim 11, wherein said encapsulate is at least one member selected from the group consisting of medications, pesticides, vitamins, preservatives, flavoring agents, and mixtures thereof.

16. The composition of claim 11, wherein said encapsulate is a flavoring agent.

17. The composition of claim 16, wherein said flavoring agent is at least one member selected from the group consisting of natural extracts, oleoresins, essential oils, protein hydrolysates, aqueous reaction flavors, compounded natural flavors, artificial flavors, and mixtures thereof.

18. The composition of claim 16, wherein said flavoring agent comprises a plasticizer or an emulsifier.

19. The composition of claim 11, wherein said extruder is a twin screw extruder.

20. The composition of claim 11, wherein said matrix (B) comprises:

(a) 50 to 99% by weight, based on the total weight of said matrix (B), of gum arabic and 1 to 50% by weight, based on the total weight of said matrix (B), of a low molecular weight carbohydrate or polyol.

21. The composition of claim 11, wherein said matrix (B) comprises:

(a) 60 to 80% by weight, based on the total weight of said matrix (B), of gum arabic and 20 to 40% by weight, based on the total weight of said matrix (B), of a low molecular weight carbohydrate or polyol.

22. The composition of claim 11, wherein said matrix (B) comprises:

(b) 50 to 99% by weight, based on the total weight of said matrix (B), of a mixture of at least two food polymers selected from the group consisting of gum arabic, hydrolyzed gelatin, gelatin, and larch gum and 1 to 50% by weight, based on the total weight of said matrix (B), of a low molecular weight carbohydrate or polyol.

23. The composition of claim 11, wherein said matrix (B) comprises:

(b) 60 to 80% by weight, based on the total weight of said matrix (B), of a mixture of at least two food polymers selected from the group consisting of gum arabic, hydrolyzed gelatin, gelatin, and larch gum and 20 to 40% by weight, based on the total weight of said matrix (B), of a low molecular weight carbohydrate or polyol.

24. The composition of claim 11, having a glass transition temperature of at least 35° C.

25. The composition of claim 11, wherein said encapsulate is present in an amount of 4 to 18% by weight, based on the total weight of said composition.

26. The composition of claim 11, wherein said encapsulate is present in an amount of 9 to 16% by weight, based on the total weight of said composition.

27. The composition of claim 1, wherein said encapsulate is present in an amount of 4 to 18% by weight, based on the total weight of said composition.

28. The composition of claim 1, wherein said encapsulate is present in an amount of 9 to 16% by weight, based on the total weight of said composition.

* * * * *